United States Patent
Matteucci et al.

(10) Patent No.: US 11,667,776 B2
(45) Date of Patent: *Jun. 6, 2023

(54) FIBER WITH ODOR CONTROL COMPONENT

(71) Applicant: Dow Global Technologies LLC, Midland, MI (US)

(72) Inventors: Scott T. Matteucci, Midland, MI (US); Jeffrey E. Bonekamp, Midland, MI (US); Arkady L. Krasovskiy, Lake Jackson, TX (US); Kefu Sun, Lake Jackson, TX (US); Keran Lu, Lake Jackson, TX (US); Ronald Wevers, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/958,895

(22) PCT Filed: Aug. 26, 2019

(86) PCT No.: PCT/US2019/048091
§ 371 (c)(1),
(2) Date: Jun. 29, 2020

(87) PCT Pub. No.: WO2020/046787
PCT Pub. Date: Mar. 5, 2020

(65) Prior Publication Data
US 2021/0363334 A1    Nov. 25, 2021

Related U.S. Application Data

(60) Provisional application No. 62/725,367, filed on Aug. 31, 2018.

(51) Int. Cl.
*D01F 6/04* (2006.01)
*A61L 15/46* (2006.01)
*C08L 23/06* (2006.01)
*A61L 15/18* (2006.01)
*A61L 15/24* (2006.01)
*D01F 1/10* (2006.01)
*C08L 23/08* (2006.01)
*C08K 3/22* (2006.01)

(52) U.S. Cl.
CPC ............. *C08L 23/06* (2013.01); *A61L 15/18* (2013.01); *A61L 15/24* (2013.01); *A61L 15/46* (2013.01); *D01F 1/10* (2013.01); *D01F 6/04* (2013.01); *C08K 2003/2248* (2013.01); *C08K 2003/2296* (2013.01); *C08L 23/0815* (2013.01); *C08L 2203/12* (2013.01); *C08L 2205/025* (2013.01)

(58) Field of Classification Search
CPC .......... C08L 23/06; C08L 23/08; C08L 23/16; C08L 33/02; C08K 2003/2296; C08K 2003/22489

See application file for complete search history.

(56) References Cited

U.S. PATENT DOCUMENTS

| | | | |
|---|---|---|---|
| 4,385,632 A | 5/1983 | Odelhog | |
| 4,435,540 A * | 3/1984 | Kishida | C08F 2/44 524/789 |
| 5,306,487 A | 4/1994 | Karapasha et al. | |
| 5,409,765 A | 4/1995 | Boettcher et al. | |
| 5,429,628 A | 7/1995 | Trinh et al. | |
| 5,540,992 A * | 7/1996 | Marcher | D01F 8/06 442/364 |
| 5,591,146 A | 1/1997 | Hasse | |
| 5,677,383 A | 10/1997 | Chum et al. | |
| 5,714,445 A | 2/1998 | Trinh et al. | |
| 5,733,272 A | 3/1998 | Brunner et al. | |
| 5,882,519 A | 3/1999 | Chou et al. | |
| 5,944,704 A | 8/1999 | Guarracino et al. | |
| 6,080,908 A | 6/2000 | Guarracino et al. | |
| 6,111,023 A | 8/2000 | Chum et al. | |
| 6,147,028 A | 11/2000 | Rizzi | |
| 6,479,150 B1 | 11/2002 | Liu et al. | |
| 6,933,420 B1 | 8/2005 | Corzani | |
| 6,984,695 B2 | 1/2006 | Brown et al. | |
| 8,093,199 B2 | 1/2012 | Johnson et al. | |
| 8,217,220 B2 | 7/2012 | Berland et al. | |
| 9,555,150 B2 | 1/2017 | Yhlen et al. | |
| 10,537,108 B2 * | 1/2020 | Kanovsky | A61K 9/7007 |
| 2004/0180189 A1 | 9/2004 | Funk et al. | |
| 2004/0224841 A1 | 11/2004 | Matusz et al. | |

(Continued)

FOREIGN PATENT DOCUMENTS

| | | |
|---|---|---|
| EP | 0515503 B1 | 10/1995 |
| EP | 97/46191 A1 | 12/1997 |
| EP | 0811387 A1 | 12/1997 |
| EP | 0811391 A1 | 12/1997 |

(Continued)

OTHER PUBLICATIONS

R. Broughton, Jr., et al., Journal of Applied Polymer Science, vol. 48, (1993), pp. 1501-1513.
H. Amid, et al., J. Mater Sci (2016) 51:4173-4200.
A. Akhmetova et al., J Would Ostomy Continence Nurs. 2016; 43(6):598-609.

*Primary Examiner* — Rip A Lee
(74) *Attorney, Agent, or Firm* — Quarles & Brady LLP

(57) ABSTRACT

The present disclosure provides a fiber and fabrics made therefrom. In an embodiment, a fiber is provided and includes an odor control composition. The odor control composition includes (A) from 85 wt % to 99.5 wt % of an olefin-based polymer and (B) from 15 wt % to 0.5 wt % of an odor suppressant. The odor suppressant includes: (i) an ionomer, (ii) particles of zinc oxide, and (iii) particles of copper oxide.

15 Claims, No Drawings

(56) References Cited

U.S. PATENT DOCUMENTS

| | | |
|---|---|---|
| 2004/0249079 A1 | 12/2004 | Funk et al. |
| 2005/0154133 A1 | 7/2005 | Engelhardt et al. |
| 2005/0165208 A1 | 7/2005 | Popp et al. |
| 2005/0287318 A1 | 12/2005 | Speer et al. |
| 2006/0155057 A1 | 7/2006 | Hermeling et al. |
| 2006/0167215 A1 | 7/2006 | Hermeling et al. |
| 2007/0043191 A1 | 2/2007 | Hermeling et al. |
| 2007/0210281 A1 | 9/2007 | Speer et al. |
| 2009/0124989 A1 | 5/2009 | Wastlund-Karlsson et al. |
| 2010/0047303 A1 | 2/2010 | Yhlen et al. |
| 2010/0221969 A1 | 9/2010 | Chen et al. |
| 2010/0300905 A1 | 12/2010 | Speer et al. |
| 2011/0054430 A1 | 3/2011 | Wastlund-Karlsson |
| 2013/0025073 A1 | 1/2013 | Souter et al. |
| 2013/0164467 A1 | 6/2013 | Speer et al. |
| 2013/0331260 A1 | 12/2013 | Hoeller et al. |
| 2014/0011912 A1 | 1/2014 | Petry |
| 2014/0248811 A1 | 9/2014 | Degroot et al. |
| 2014/0248816 A1 | 9/2014 | Bonavoglia et al. |
| 2015/0084230 A1 | 3/2015 | Kuroda et al. |
| 2018/0222087 A1 | 8/2018 | Tijhuis et al. |
| 2018/0362232 A1 | 12/2018 | Spigaroli et al. |
| 2021/0363337 A1 * | 11/2021 | Krasovskiy .......... C08L 23/0815 |
| 2022/0162400 A1 | 5/2022 | Gou et al. |
| 2022/0193956 A1 | 6/2022 | Huang et al. |

FOREIGN PATENT DOCUMENTS

| | | |
|---|---|---|
| EP | 0813848 A1 | 12/1997 |
| EP | 0891708 A1 | 1/1999 |
| EP | 0515473 B1 | 4/1999 |
| EP | 0749295 B1 | 7/2000 |
| WO | 96/06589 A1 | 3/1996 |
| WO | 97/46187 A1 | 12/1997 |
| WO | 97/46192 A1 | 12/1997 |
| WO | 98/26808 A2 | 6/1998 |
| WO | 02/052084 A2 | 7/2002 |
| WO | 2008/058565 A1 | 5/2008 |
| WO | 2008/138386 A1 | 11/2008 |
| WO | 2010040418 A1 | 4/2010 |
| WO | WO 2016/125132 A1 * | 8/2016 ............... C08K 3/22 |

* cited by examiner

FIBER WITH ODOR CONTROL COMPONENT

BACKGROUND

Hygiene articles, such as incontinence garments, feminine care products, and diapers require a high degree of odor control. Many such hygiene articles include fibers and/or fabric components for moisture absorption and/or odor control.

Odor control particles such as zeolites, sodium bicarbonate, activated silica, activated carbon, and metal oxides (such as zinc oxide (ZnO)), and zinc salts in particular, are known to consume many odor-generating molecules such as urea (and other amino-based odorants), $H_2S$ and mercaptans that are typically arise during use of a hygiene article. All other factors being equal, it is known that ZnO concentration, for example, and odor suppression are directly related—i.e., as ZnO concentration increases in a given olefin-based polymer article, the effectiveness of odor suppression also increases.

Although odor suppression increases as metal oxide (ZnO in particular) increases, limits do exist for the amount of ZnO that can be effectively incorporated into olefin-based polymer structures such as films and fibers. High loading of ZnO particles in polymeric films increases extrusion die lip buildup, thereby causing film defects. High loading of ZnO particles also increases haze, resulting in degradation of olefin-based polymer film transparency and/or degradation in film color. High loading of ZnO particles also deleteriously impacts mechanical properties such as impact strength and film tear strength. Processing parameters and end-use mechanical requirements thereby impose practical limits to the load of odor absorbers, such as ZnO particles, into olefin-based polymer compositions.

The art recognizes the on-going need for new odor control formulations for fiber and fabric structures. Further recognized in the art is the need for new odor control compositions for fibers and fabrics with suitable processing and mechanical properties for hygiene articles.

SUMMARY

The present disclosure provides a fiber. In an embodiment, a fiber is provided and includes an odor control composition. The odor control composition includes (A) from 85 wt % to 99.5 wt % of an olefin-based polymer and (B) from 15 wt % to 0.5 wt % of an odor suppressant. The odor suppressant includes: (i) an ionomer, (ii) particles of zinc oxide, and (iii) particles of copper oxide.

The present disclosure provides a fabric. In an embodiment, a fabric is provided and includes a plurality of fibers. The fibers include (A) from 85 wt % to 99.5 wt % of an olefin-based polymer and (B) from 15 wt % to 0.5 wt % of an odor suppressant. The odor suppressant includes a blend of: (i) an ionomer, (ii) particles of zinc oxide, and (iii) particles of copper oxide.

Definitions

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2, or 3 to 5, or 6, or 7), any subrange between any two explicit values is included (e.g., the range 1-7 above includes subranges of 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

An "agglomerate" is a plurality of individual fine solid particles clumped or otherwise together forming a single mass.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

An "ethylene-based polymer" is a polymer that contains more than 50 weight percent (wt %) polymerized ethylene monomer (based on the total amount of polymerizable monomers) and, optionally, may contain at least one comonomer. Ethylene-based polymer includes ethylene homopolymer, and ethylene copolymer (meaning units derived from ethylene and one or more comonomers). The terms "ethylene-based polymer" and "polyethylene" may be used interchangeably. Non-limiting examples of ethylene-based polymer (polyethylene) include low density polyethylene (LDPE) and linear polyethylene. Non-limiting examples of linear polyethylene include linear low density polyethylene (LLDPE), ultra-low density polyethylene (ULDPE), very low density polyethylene (VLDPE), multi-component ethylene-based copolymer (EPE), ethylene/α-olefin multi-block copolymers (also known as olefin block copolymer (OBC)), substantially linear, or linear, plastomers/elastomers, and high density polyethylene (HDPE). Generally, polyethylene may be produced in gas-phase, fluidized bed reactors, liquid phase slurry process reactors, or liquid phase solution process reactors, using a heterogeneous catalyst system, such as Ziegler-Natta catalyst, a homogeneous catalyst system, comprising Group 4 transition metals and ligand structures such as metallocene, non-metallocene metal-centered, heteroaryl, heterovalent aryloxyether, phosphinimine, and others. Combinations of heterogeneous and/or homogeneous catalysts also may be used in either single reactor or dual reactor configurations.

"Ethylene plastomers/elastomers" are substantially linear, or linear, ethylene/α-olefin copolymers containing homogeneous short-chain branching distribution comprising units derived from ethylene and units derived from at least one $C_3$-$C_{10}$ α-olefin comonomer. Ethylene plastomers/elastomers have a density from 0.870 g/cc to 0.917 g/cc. Non-limiting examples of ethylene plastomers/elastomers include AFFINITY™ plastomers and elastomers (available from The Dow Chemical Company), EXACT™ Plastomers (available from ExxonMobil Chemical), Tafmer™ (available from Mitsui), Nexlene™ (available from SK Chemicals Co.), and Lucene™ (available LG Chem Ltd.).

"High density polyethylene" (or "HDPE") is an ethylene homopolymer or an ethylene/α-olefin copolymer with at least one $C_4$-$C_{10}$ α-olefin comonomer, or $C_4$-$C_8$ α-olefin comonomer and a density from 0.940 g/cc, or 0.945 g/cc, or 0.950 g/cc, 0.953 g/cc to 0.955 g/cc, or 0.960 g/cc, or 0.965 g/cc, or 0.970 g/cc, or 0.975 g/cc, or 0.980 g/cc. The HDPE can be a monomodal copolymer or a multimodal copolymer. A "monomodal ethylene copolymer" is an ethylene/$C_4$-$C_{10}$ α-olefin copolymer that has one distinct peak in a gel permeation chromatography (GPC) showing the molecular weight distribution. A "multimodal ethylene copolymer" is an ethylene/$C_4$-$C_{10}$ α-olefin copolymer that has at least two distinct peaks in a GPC showing the molecular weight distribution. Multimodal includes copolymer having two peaks (bimodal) as well as copolymer having more than two peaks. Non-limiting examples of HDPE include DOW™ High Density Polyethylene (HDPE) Resins (available from The Dow Chemical Company), ELITE™ Enhanced Polyethylene Resins (available from The Dow Chemical Company), CONTINUUM™ Bimodal Polyethylene Resins (available from The Dow Chemical Company), LUPOLEN™ (available from Lyondell-Basell), as well as HDPE products from Borealis, Ineos, and ExxonMobil.

An "interpolymer" is a polymer prepared by the polymerization of at least two different monomers. This generic term includes copolymers, usually employed to refer to polymers prepared from two different monomers, and polymers prepared from more than two different monomers, e.g., terpolymers, tetrapolymers, etc.

"Linear low density polyethylene" (or "LLDPE") is a linear ethylene/α-olefin copolymer containing heterogeneous short-chain branching distribution comprising units derived from ethylene and units derived from at least one $C_3$-$C_{10}$ α-olefin, or $C_4$-$C_8$ α-olefin, comonomer. LLDPE is characterized by little, if any, long chain branching, in contrast to conventional LDPE. LLDPE has a density from 0.910 g/cc to less than 0.940 g/cc. Non-limiting examples of LLDPE include TUFLIN™ linear low density polyethylene resins (available from The Dow Chemical Company), DOWLEX™ polyethylene resins (available from the Dow Chemical Company), and MARLEX™ polyethylene (available from Chevron Phillips).

"Low density polyethylene" (or "LDPE") consists of ethylene homopolymer, or ethylene/α-olefin copolymer comprising at least one $C_3$-$C_{10}$ α-olefin, or $C_4$-$C_8$α-olefin, that has a density from 0.915 g/cc to less than 0.940 g/cc and contains long chain branching with broad MWD. LDPE is typically produced by way of high pressure free radical polymerization (tubular reactor or autoclave with free radical initiator). Non-limiting examples of LDPE include Mar-Flex™ (Chevron Phillips), LUPOLEN™ (LyondellBasell), as well as LDPE products from Borealis, Ineos, ExxonMobil, and others.

"Multi-component ethylene-based copolymer" (or "EPE") comprises units derived from ethylene and units derived from at least one $C_3$-$C_{10}$ α-olefin, or $C_4$-$C_8$ α-olefin, comonomer, such as described in patent references U.S. Pat. Nos. 6,111,023; 5,677,383; and 6,984,695. EPE resins have a density from 0.905 g/cc to 0.962 g/cc. Non-limiting examples of EPE resins include ELITE™ enhanced polyethylene (available from The Dow Chemical Company), ELITE AT™ advanced technology resins (available from The Dow Chemical Company), SURPASS™ Polyethylene (PE) Resins (available from Nova Chemicals), and SMART™ (available from SK Chemicals Co.).

An "olefin-based polymer" or "polyolefin" is a polymer that contains more than 50 weight percent polymerized olefin monomer (based on total amount of polymerizable monomers), and optionally, may contain at least one comonomer. Non-limiting examples of an olefin-based polymer include ethylene-based polymer or propylene-based polymer.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "propylene/α-olefin polymer" are indicative of copolymer as described above prepared from polymerizing ethylene or propylene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to has being based on "units" that are the polymerized form of a corresponding monomer.

A "propylene-based polymer" is a polymer that contains more than 50 weight percent polymerized propylene monomer (based on the total amount of polymerizable monomers) and, optionally, may contain at least one comonomer. Propylene-based polymer includes propylene homopolymer, and propylene copolymer (meaning units derived from propylene and one or more comonomers). The terms "propylene-based polymer" and "polypropylene" may be used interchangeably. Non-limiting examples of suitable propylene copolymer include propylene impact copolymer and propylene random copolymer.

"Ultra-low density polyethylene" (or "ULDPE") and "very low density polyethylene" (or "VLDPE") each is a linear ethylene/α-olefin copolymer containing heterogeneous short-chain branching distribution comprising units derived from ethylene and units derived from at least one $C_3$-$C_{10}$ α-olefin comonomer. ULDPE and VLDPE each has a density from 0.885 g/cc to 0.915 g/cc. Non-limiting examples of ULDPE and VLDPE include ATTANE™ ultra low density polyethylene resins (available from The Dow Chemical Company) and FLEXOMER™ very low density polyethylene resins (available from The Dow Chemical Company).

Test Methods

D10, D50, and D90 particle size is measured using a Coulter LS 230 Laser Light Scattering Particle Sizer, available from Coulter Corporation. D10 particle size is the particle diameter at which 10% of the powder's mass is composed of particles with a diameter less than this value. D50 particle size is the particle diameter at which 50% of the powder's mass is composed of particles with a diameter less than this value and 50% of the powder's mass is composed of particles with a diameter greater than said value. D90 particle size is the particle diameter at which 90% of the powder's mass is composed of particles with a diameter less than this value. Mean volume average particle size is measured using a Coulter LS 230 Laser Light Scattering Particle Sizer, available from Coulter Corporation. Particle size distribution is calculated in accordance with Equation A:

$$\text{Particle size distribution} = \frac{(D90 - D10)}{D50}. \quad \text{Equation A}$$

Dart impact strength is measured in accordance with ASTM D1709, with results reported in grams (g).

Denier is a unit of measure for the linear mass density of fibers, with units of g/9000 m of fiber.

Density is measured in accordance with ASTM D792, Method B. The result is recorded in grams per cubic centimeter (g/cc).

Differential Scanning calorimetry (DSC). Differential Scanning calorimetry (DSC) can be used to measure the melting, crystallization, and glass transition behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (about 25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 180° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are extrapolated onset of melting, Tm, and extrapolated onset of crystallization, Tc. Heat of fusion ($H_f$) (in Joules per gram), and the calculated % crystallinity for polyethylene samples using the following Equation: % Crystallinity=(($H_f$)/292 J/g)×100. Glass transition temperature, Tg, is determined from the DSC heating curve where half the sample has gained the liquid heat capacity as described in Bernhard Wunderlich, *The Basis of Thermal Analysis, in Thermal Characterization of Polymeric Materials* 92, 278-279 (Edith A. Turi ed., 2d ed. 1997). Baselines are drawn from below and above the glass transition region and extrapolated through the Tg region. The temperature at which the sample heat capacity is half-way between these baselines is the Tg.

Elmendorf tear (or tear) is measured in accordance with ASTM D1922-15, machine direction (MD), with results reported in grams-force (gf).

Melt flow rate (MFR) in g/10 min is measured in accordance with ASTM D1238 (230° C./2.16 kg).

Melt index (MI) (12) in g/10 min is measured in accordance with ASTM D1238 (190° C./2.16 kg).

Odor Suppression/Odor Suppression Value.

Odor suppression is the ability of a composition to neutralize, or otherwise reduce, the amount of volatile sulfur-containing compounds. In the present disclosure, the odor suppression for methyl mercaptan is measured with gas chromatography equipped with an Agilent Sulfur Chemiluminescence Detector (GC-SCD) in accordance with ASTM D5504-12. A control sample is prepared by placing a film formed from DOWLEX™ 2085G, ethylene/octene LLDPE, into a Tedlar® bag (polyvinyl fluoride). The Tedlar® bag for the control is subsequently filled with 900 mL of helium gas and known amounts of methyl mercaptan, and the Tedlar® bag is closed. Test samples are prepared by placing a film formed from respective test compositions, each test film placed into a respective Tedlar® bag. Each Tedlar® bag is subsequently filled with 900 mL of helium gas and known amount of methyl mercaptan, and the Tedlar® bag is closed. Samples are injected onto the GC-SCD at pre-determined time intervals from each bag in order to evaluate odor suppression capability.

The reference samples and test samples were analyzed after two days. The reference sample was used as the calibration standard to calculate the methyl mercaptan concentration of each test sample.

A. Sample Preparation

The control sample and each test sample containing 5 ppmv methyl mercaptan were prepared in SKC 1 L sample bag (SKC Tedlar® Sample Bag, 1 Liter, Cat No. 232-01). A reference sample without a film was prepared in a Tedlar® bag as the calibration standard.

1. Cut 1.0 g of film into strips (approximately 1 cm×30 cm).
2. Unscrew the valve from the sample bag, insert the film strips into the bag through the valve opening with the handle of cotton tipped applicator, and install the valve back to the sample bag, squeeze air out of bag before tightening the valve to seal the bag.
3. Fill the bag with 0.90 L of helium gas (AirGas, Ultra Grade Helium).
4. Inject 50 mL of 100 ppmv methyl mercaptan, into the bag using a gas-tight glass syringe.

The odor suppression value test can also be performed for other odorants, including ethyl mercaptan, propyl mercaptan, and butyl mercaptan.

B. GC-SCD Conditions
 1 Gas chromatograph: Agilent Model 7890 with a split/splitless injection port, available from Agilent Technologies, 2850 Centerville Road, Wilmington, Del. 19808.
 2. Detector: Agilent Sulfur Chemiluminescence (SCD), Model G6644A.
 3. Chromatography data system: Agilent OpenLAB software.
 4. Columns: Agilent J&W DB-1 30 m×0.32 mm ID, 5 μm film thickness.
 5. Carrier Gas: Hydrogen, constant flow mode, 2.0 mL/min.

6. Inlet: Split, temperature: 250° C., split ratio: 100:1.
7. Injection volume: 500 μL by Valco Six Port Valve, Loop Size: 500 μL.
8. Oven Temperature: 30° C. hold for 1 minute, 15° C./min to 140° C., hold for 1 minutes.
9. SCD Detector Conditions:
Temperature: 250° C.
Hydrogen Flow: 38.3 mL/min.
Oxidizer Flow: 59.9 sccm.
Pressure: 400 Torr.

An odor suppression value (OSV) is the removal % of methyl mercaptan calculated by the following equation:

$$OSV = \frac{\text{Concentration of Reference Sample} - \text{Concentration of Test Sample}}{\text{Concentration of Reference Sample}} \times 100$$

$$= \frac{\text{Peak Area of Reference Sample} - \text{Peak Area of Test Sample}}{\text{Peak Area of Reference Sample}} \times 100$$

The Peak Area is the response of GC-SCD.

A non-limiting example of OSV calculation is provided. At two days the GC-SCD peak area of methylmercaptan in the reference sample is 28240298, whereas the GC-SCD peak area of methyl mercaptan in the test sample IE 1 is 5667327 (unit is pA*s in Agilent OpenLAB software). The odor suppression value for the test sample IE 1 is (((28240298−5667327)/28240298)*100=80. As shown in the equation of OSV, both concentration of methyl mercaptan and GC-SCD Peak Area of methyl mercaptan can be used to calculate OSV.

Porosity and Surface Area. Brunauer-Emmett-Teller (BET) porosity and surface area analysis are performed using a Micromeritics Accelerated Surface Area & Porosimetry instrument (ASAP 2420). The sample is out-gassed at 105° C. while under vacuum prior to analysis.

The ASAP 2420 instrument employs a static (volumetric) method of dosing samples and measures the quantity of gas that can be physically adsorbed (physisorbed) on a solid at liquid nitrogen temperature. For the multi-point BET measurement the volume of nitrogen uptake is measured at pre-selected relative pressure points at constant temperature. The relative pressure is the ratio of the applied nitrogen pressure to the vapor pressure of nitrogen at the analysis temperature of 77 Kelvin (K). Results for porosity are reported in cubic meters per gram, or m$^3$/g. Results for surface area are reported in square meters per gram, or m$^2$/g.

The term "ramp-to-break" refers to the drawing speed, in meters per minute (or mpm), at which the fiber completely breaks down and is discontinuous. Ramp-to-break is a method for determining the maximum line speed for drawing down fibers on the Hills line as achieved by gradually increasing the take up speed of the filament bundle. This is accomplished with a ramping method to a point where at least one fiber break occurs. The highest speed that a material can be run for a minimum of 30 seconds without a single fiber break is the maximum draw down speed or ramp-to-break speed. The ramping procedure starts at 1500 mpm winding speed—or lower, if necessary. The material is run at this line speed for 30 seconds and if no fiber breaks are observed then the godet roll speed is increased by 250 mpm over 30 seconds. The material is run for 30 seconds at each interim point while checking for breaks. This is done until a break is achieved. The speed at which the break occurs is recorded. The process is repeated a minimum of three times and the average is recorded as the maximum draw down speed via the ramp-to-break methodology. The standard deviation for repeat measurements on the same polymer is ca 100 mpm.

The term "tenacity" refers to the ratio of load required to break a fiber and the denier of the fiber, measured in accordance with ASTM D3217-07.

The term "tensile strength" refers to the maximum amount of tensile stress that a fiber can withstand before breaking, measured in accordance with ASTM D76M-11 (2016).

Zinc/copper—total amount. The total amount of zinc and/or copper present in a composition is determined with x-ray fluorescence spectrometry (XRS), in accordance with ASTM D6247. Results are reported in parts per million, or ppm.

DETAILED DESCRIPTION

The present disclosure provides a fiber. In an embodiment, a fiber is provided and includes an odor control composition. The odor control composition includes: (A) from 85 wt % to 99.5 wt % of an olefin-based polymer, and (B) from 15 wt % to 0.5 wt % of an odor suppressant comprising a blend of: (i) an ionomer; (ii) particles of zinc oxide; and (iii) particles of copper oxide.

Fiber

A "fiber" is a single, continuous strand of elongated material having a generally round cross-section and a length to diameter ratio of greater than 10.

Odor Control Composition

The present fiber includes an odor control composition. In an embodiment, the odor control composition includes from 85 wt %, or 90 wt % to 95 wt %, or 97 wt %, 99 wt %, or 99.5 wt % component (A) that is an olefin-based polymer. The odor control composition includes a reciprocal amount of component (B), or from 15 wt %, or 10 wt % to 5 wt %, or 3 wt %, 1 wt % or 0.5 wt % of an odor suppressant.

The odor control composition has an odor suppression value from 45%, or 46%, or 50%, or 60%, or 70% to 75%, or 80%, or 85%, or 90%, as measured in accordance with ASTM D5504-12.

A. Olefin-Based Polymer

The present composition includes an olefin-based polymer. The olefin-based polymer can be a propylene-based polymer or an ethylene-based polymer. Non-limiting examples of propylene-based polymer include propylene copolymer, propylene homopolymer, and combinations thereof. In an embodiment, the propylene-based polymer is a propylene/α-olefin copolymer. Non-limiting examples of suitable α-olefins include $C_2$ and $C_4$-$C_{20}$ α-olefins, or $C_4$-$C_{10}$ α-olefins, or $C_4$-$C_8$ α-olefins. Representative α-olefins include ethylene, 1-butene, 1-pentene, 1-hexene, 1-heptene and 1-octene.

In an embodiment, the propylene/α-olefin copolymer is a propylene/ethylene copolymer containing greater than 50 wt % units derived from propylene, or from 51 wt %, or 55 wt %, or 60 wt % to 70 wt %, or 80 wt %, or 90 wt %, or 95 wt %, or 99 wt % units derived from propylene, based on the weight of the propylene/ethylene copolymer. The propylene/ethylene copolymer contains a reciprocal amount of units derived from ethylene, or from less than 50 wt %, or 49 wt %, or 45 wt %, or 40 wt % to 30 wt %, or 20 wt %, or 10 wt %, or 5 wt %, or 1 wt % units derived from ethylene, based on the weight of the propylene/ethylene copolymer.

In an embodiment, the olefin-based polymer is an ethylene-based polymer. The ethylene-based polymer can be an ethylene homopolymer or an ethylene/α-olefin copolymer.

In an embodiment, the ethylene-based polymer is an ethylene/α-olefin copolymer. Non-limiting examples of suitable α-olefins include $C_3$-$C_{20}$ α-olefins, or $C_4$-$C_{10}$ α-olefins, or $C_4$-$C_8$ α-olefins. Representative α-olefins include propylene, 1-butene, 1-pentene, 1-hexene, 1-heptene and 1-octene.

In an embodiment, the ethylene/α-olefin copolymer is an LLDPE that is an ethylene/$C_4$-$C_8$ α-olefin copolymer. The LLDPE has one, some, or all of the following properties:

(i) a density from 0.910 g/cc to 0.930 g/cc, or from 0.915 g/cc to 0.926 g/cc; and/or (ii) a melt index from 0.5 g/10 min, or 1.0 g/10 min, or 2.0 g/10 min to 3.0 g/10 min, or 4.0 g/10 min, or 5.0 g/10 min.

B. Odor Suppressant

The present composition includes an odor suppressant. The odor suppressant is composed of a (Bi) an ionomer, (Bii) particles of zinc oxide, and (Biii) particles of copper oxide.

(Bi) Ionomer

The present composition includes an ionomer. An "ionomer," as used herein, is an ion-containing polymer. An "ion" is an atom that has an electrical charge, either positive or negative. The ionomer has a majority weight percent (generally 85% to 90%) of repeating monomer units that are non-ionic (non-polar), and a minority weight percent (generally 10% to 15%) of repeating comonomer units that are ionic, or polar (i.e., positively-charged or negatively-charged). The positive charges of the ionic groups attract the negative charges of the ionic groups, creating ionic bonds. Ionomer resins exhibit what is known as "reversible cross-linking" behavior, i.e. when an ionomer is heated, the polymer chains have increased mobility, and the ionic bonds cannot stay intact because the positive charges and negative charges are pulled away from each other.

Non-limiting examples of the monomers and comonomers from which an ionomer is derived include a copolymer of at least one alpha-olefin and at least one ethylenically unsaturated carboxylic acid and/or anhydride. Non-limiting examples of suitable alpha-olefins include ethylene, propylene, 1-butene, 1-pentene, 1-hexene, 1-heptene, 1-octene, and 3-methylbutene. Non-limiting examples of suitable carboxylic acids and anhydrides include acrylic acid, methacrylic acid, ethacrylic acid, maleic acid, fumaric acid, and maleic anhydride.

In an embodiment, the ionomer is a copolymer of ethylene and methacrylic acid.

In an embodiment, the ionomer is a copolymer of ethylene and acrylic acid.

In an embodiment, the ionomer is a metal ionomer. A "metal ionomer," as used herein, refers to a copolymer based on a metal salt of a copolymer of an alpha-olefin and an ethylenically unsaturated carboxylic acid and/or anhydride. The metal ionomer may be fully or partially neutralized by a metal ion. Non-limiting examples of metals suitable for neutralizing an ionomer include the alkali metals, i.e., cations such as sodium, lithium, and potassium; alkaline earth metals, i.e., cations such as calcium, magnesium; and transition metals such as zinc. A non-limiting example of a metal ionomer is Surlyn® 8660, which is a sodium salt of an ethylene and methacrylic acid copolymer, available from Dow-DuPont.

In an embodiment, the metal ionomer is a zinc ionomer. The term "zinc ionomer," (or "ZnI/O") as used herein, refers to a copolymer based on a zinc salt of a copolymer of ethylene and a vinyl comonomer with carboxylic acid/or anhydride. Non-limiting examples of suitable comonomer having vinyl comonomer with an acid group include methyl/methacrylic acid, vinyl acrylic acid, methacrylate, n-butyl acrylic acid, and acrylic acid.

Non-limiting examples of suitable zinc ionomer include zinc salt of ethylene/acrylic acid comonomer, zinc salt of ethylene/methyl-methacrylic acid copolymer, zinc salt of ethylene/vinyl acrylic acid copolymer, zinc salt of ethylene/methacrylate copolymer, zinc salt of ethylene/n-butyl acrylic acid copolymer, and any combination thereof.

In an embodiment, the zinc ionomer is a zinc salt of ethylene/acrylic acid copolymer. Non-limiting examples of a suitable zinc ionomer include Surlyn® 9150, which is a zinc salt of an ethylene and methacrylic acid copolymer, available from Dow-DuPont.

B(ii) Particles of Zinc Oxide

The odor suppressant includes particles of zinc oxide (or "ZnO"). The ZnO particles have a D50 particle size from 100 nm to 3000 nm, a surface area from 1 $m^2$/g to less than 10 $m^2$/g, and a porosity less than 0.020 $m^3$/g.

In an embodiment, the ZnO particles have one, some, or all of the following properties (i)-(iii) below:

(i) a particle size D50 from 100 nm, or 200 nm, or 300 nm, or 400 nm to 500 nm, or 600 nm, or 700 nm, or 800 nm, or 900 nm, or 1000 nm, or 2000 nm, or 3000 nm; and/or (ii) a surface area from 1 $m^2$/g, or 2 $m^2$/g, or 3 $m^2$/g, or 4 $m^2$/g to 5 $m^2$/g, or 6 $m^2$/g, or 7 $m^2$/g, or 8 $m^2$/g, or 9 $m^2$/g; and/or (iii) a porosity from 0.005 $m^3$/g, or 0.006 $m^3$/g, or 0.008 $m^3$/g, or 0.010 $m^3$/g to 0.012 $m^3$/g, or 0.013 $m^3$/g, or 0.015 $m^3$/g, or less than 0.020 $m^3$/g.

Non-limiting examples of suitable ZnO particles include 800HSA (Zinc Oxide, LLC), ZnO micropowder (US Research Nanomaterials), and Zoco102 (Zochem, Inc.).

(Biii) Particles of Copper Oxide

The odor suppressant also includes particles of copper oxide. The copper oxide can be either "$Cu_2O$" (copper I oxide) or "CuO" (copper II oxide), or a mix of both. In an embodiment, the copper oxide particles have a D50 particle size from 100 nm to 3000 nm and a surface area from 1 $m^2$/g to less than 10 $m^2$/g. Bounded by no particular theory, it is believed that the copper oxide particles contribute as a sulfur scavenger for hydrogen sulfide and mercaptans in particular.

In an embodiment, the copper oxide particles have a particle size D50 from 100 nm, or 200 nm, or 300 nm, or 400 nm to 500 nm, or 600 nm, or 700 nm, or 800 nm, or 900 nm, or 1000 nm, or 2000 nm, or 3000 nm. Non-limiting examples of suitable copper oxide particles include $Cu_2O$ 325 mesh powder and CuO 325 mesh powder available from Reade Advanced Materials.

C. Composition

The present composition includes (A) from 85 wt % to 99.5 wt % of the olefin-based polymer and (B) from 15 wt % to 0.5 wt % of the odor suppressant, based on total weight of the composition (hereafter, Composition 1). The odor suppressant is mixed, or otherwise blended, into the olefin-based polymer matrix, and is a blend of (Bi) an ionomer, (Bii) particles of zinc oxide, and (Biii) particles of copper oxide. The composition has an odor suppression value of greater than 45%. In an embodiment, the composition has an odor suppression value from 46%, or 49%, or 50% or 60% or 70% to 75%, or 80%, or 85%, or 90%.

The ZnI/O (Bi) is present in component (B) in an amount of 1 to 90 wt % based on the total weight of component (B). The ratio of ZnO to ZnI/O (hereafter "ZnO to ZnI/O ratio") is from 3:1 to 1:7 based on the total weight of the odor suppressant (B). The ZnO to ZnI/O ratio can be from 3:1, or 2:1, or 1:1 to 1:2, or 1:3, or 1:4, or 1:5, or 1:6, or 1:7. The particles of copper oxide (Biii) are present in component (B) in an amount of from 0.01 wt % to 30 wt % based on the total weight of component (B). The particles of copper oxide can be copper (I) oxide ($Cu_2O$), copper (II) oxide (CuO), or a mix of both. In an embodiment, the weight percent ratio between the ionomer (Bi), the zinc oxide (Bii), and the copper oxide (Biii) is from 150:100:1 to 2.9:2.5:1 based on the total weight of the odor suppressant (B) (hereafter, Composition 1).

In an embodiment, the weight percent ratio between the ionomer (Bi), the zinc oxide (Bii), and the copper oxide (Biii) is from 100:75:1 to 3:2.5:1 based on the total weight of the odor suppressant (B).

In an embodiment, the present composition includes from 85 wt %, or 90 wt % to 95 wt %, or 97 wt %, 99 wt %, or 99.4 wt %, or 99.5 wt % component (A) that is an ethylene-based polymer. The present composition includes a reciprocal amount of the odor suppressant, component (B), or from 15 wt %, or 10 wt % to 5 wt %, or 3 wt %, 1 wt %, or 0.6 wt %, or 0.5 wt % odor suppressant wherein Zn I/O to ZnO to $Cu_2O$ ratio is from 12.5:12.5:1 to 2.5:2.5:1. The odor suppressant (B) can be any odor suppressant as previously disclosed herein (hereafter, Composition 2).

The composition (i.e. Composition 1 and/or Composition 2) has an odor suppression value from 46%, or 50%, or 60%, or 70% to 75%, or 80%, or 85%, or 90%.

While the combination of ZnO and ionomer improve OSV for methyl mercaptan, the addition of copper oxide, and in particular $Cu_2O$, has been observed to further improve overall OSV. In fact, Applicant surprisingly discovered that the addition of from 0.01 wt % to 0.1 wt % of $Cu_2O$ to a ZnO/ionomer odor suppressing composition (based on the total weight of odor suppressant composition (B), for example) can more than double the OSV performance compared to ZnO/ionomer odor suppressing compositions that lack the copper oxide particles.

D. Blend

Components (A) and (B) are mixed, or otherwise blended, together to form the present composition so that the particles of zinc oxide and the particles of copper oxide are (i) dispersed within the olefin-based polymer (A) and/or (i) dispersed within the ionomer (Bi).

In an embodiment, the present composition is produced as an odor control masterbatch wherein component (B) is formed by dispersing the zinc oxide particles (Bii) and the copper oxide particles (Biii) into the ionomer (Bi). The dispersing may be accomplished by physical mixing and/or melt blending of components (Bi), (Bii), and (Biii) in order to uniformly disperse the particles (zinc oxide and copper oxide) throughout the ionomer. The resultant component (B) is subsequently mixed, or otherwise blended, with the olefin-based polymer, component (A). The mixing of component (B) and component (A) may be accomplished by physical mixing and/or melt blending (hereafter odor control masterbatch 1).

In an embodiment, the present composition is produced as an odor control masterbatch by dispersing the zinc oxide particles (Bii) into the ionomer (Bi). The dispersing may be accomplished by physical mixing and/or melt blending of components (Bi) and (Bii) in order to uniformly disperse the zinc particles throughout the ionomer (Bi) ("Bi-Bii blend"). The Bi-Bii blend and the copper oxide particles are subsequently added to the olefin-based polymer component (A) by physical mixing and/or melt blending to form the present composition of a homogeneous blend of olefin-based polymer (A), ionomer (Bi), zinc oxide particles (Bii), and copper oxide particles (Biii). (hereafter odor control masterbatch 2)

In an embodiment, the present composition is produced as an odor control masterbatch by mixing the ionomer (Bi), the zinc oxide particles (Bii), the copper oxide particles (Biii) and the the olefin-based polymer (A). The mixing may be accomplished by physical mixing and/or melt blending of components (A), (Bi), (Bii), and (Biii) in order to uniformly disperse the ionomer (Bi), the zinc oxide particles (Bii), and the copper oxide particles (Biii) throughout the olefin-based polymer (A) (hereafter odor control masterbatch 3).

In an embodiment, the present composition is produced as an odor control masterbatch by mixing the ionomer (Bi), the zinc oxide particles (Bii), and the olefin-based polymer (A). The mixing may be accomplished by physical mixing and/or melt blending of components (Bi), (Bii), and (A) in order to uniformly disperse (Bi) and (Bii) throughout (A) (hereafter, A-Bi-Bii blend). Copper oxide particles (Biii) are mixed with component (A). The mixing may be accomplished by physically mixing and/or melt blending in order to uniformly disperse the copper oxide particles (Biii) into (A) (hereafter, A-Biii blend). The A-Bi-Bii blend is then mixed with the A-Biii blend. The mixing may be accomplished by physical mixing and/or melt blending to form a homogeneous composition composed of olefin-based polymer (A), ionomer (Bi), zinc oxide particles (Bii), and copper oxide particles (Biii) (hereafter, odor control masterbatch 4).

In an embodiment, the odor control masterbatch (i.e., any of odor control masterbatch 1, 2, 3, or 4) includes from 20 wt % to 30 wt % ionomer, from 20 wt % to 30 wt % particles of zinc oxide, from 5 wt % to 15 wt % particles of copper oxide, and from 30 wt % to 60 wt % LLDPE, with the aggregate of the components amounting to 100 wt % odor control composition.

The present fiber may be a mono-component fiber, a homofil fiber, or a bi-component fiber.

In an embodiment, the fiber is a mono-component fiber. A "mono-component fiber" (also known as "monofiber" or "homofil fiber") is a fiber that is a continuous strand of a single material. The mono-component fiber can have either an indefinite (i.e., not predetermined) length, or a definite length (i.e., a "staple fiber" which is a discontinuous strand of material which has been cut or otherwise divided into segments of a predetermined length). A mono-component fiber is a fiber that has a single polymer region or domain, and that does not have any other distinct polymer regions (as does a bi-component fiber).

In an embodiment, the fiber is a bi-component fiber. A "bi-component fiber" is a fiber that has two or more distinct polymeric components. Bi-component fibers are also known as conjugated or multicomponent fibers. The polymers are usually different from each other although two or more components may comprise the same polymer. The polymeric components are arranged in distinct zones across the cross-section of the bi-component fiber. The different components of the bi-component fiber usually extend continuously along the length of the bi-component fiber. The configuration of a bi-component fiber can be, for example, a sheath-core arrangement (in which one polymer is surrounded by another), a segmented pie arrangement, or an "islands-in-the sea" arrangement.

The bi-component fiber includes a first component and a second component, wherein the first component is the odor control composition.

Non-limiting examples of suitable materials for the second component include olefin-based polymer (i.e. propoylene-based polymer and ethylene-based polymer), polyesters such as polyethylene terephthalate, glycol-modified polyethylene terephthalate, polybutylene terephthalate, polylactic acid, polytrimethylene terephthalate (e.g., SORONA® available from DuPont), polyethylene 2,5-furandicarboxylate, polyhydroxybutyrate, polyamide, polylactic acid (e.g., NatureWorks available from Cargill-Dow and LACEA® from Mistui Chemical), diacid/diol aliphatic polyester (e.g. BIONOLLE® 1000 and BIONELLE® 3000 available from Showa High Polymer Company, Ltd.), and aliphatic/aromatic copolyester (e.g. EASTAR™ BIO Copolyester from Eastman Chemical or ECOFLEX™ from BASF), and combinations thereof.

The polyester may have a density ranging from 1.2 g/cc to 1.5 g/cc, or from 1.35 g/cc to 1.45 g/cc.

The polyester may have a molecular weight equivalent to an intrinsic viscosity (IV) from 0.5 dl/g to 1.4 dl/g, as determined according to ASTM D4603 or ASTM D2857.

In an embodiment, the bi-component fiber has a sheath-core configuration whereby the core (composed of the second component) is either centrally or non-centrally located within the sheath (composed of the odor control composition), with the sheath completely surrounding the core.

In an embodiment, the bi-component fibers have a segmented pie configuration. The fiber is composed of a plurality of first pie segments. The first pie segments are composed of the first component that is the odor control composition. The fiber also includes a plurality of second pie segments. The second pie segments are composed of the second component. Each pie segment extends from a center point of the fiber and extends radially outward to the outer surface of the fiber. The volume of the fiber is filled by an alternating arrangement of first pie segments and second pie segments. The alternating first pie segments and second pie segments extend along the length, or along the entire length, of the fiber, and are integral and inseparable.

In an embodiment, the bi-component fibers have an "islands-in-the-sea configuration." The fiber is composed of a plurality of cores (formed from the second component). The plurality of cores are separated from each other and are disposed in a sheath composed of the first component that is the odor control composition. The plurality of cores form discrete "islands" within the "sea," which is the sheath. The material of the sheath (the odor control composition, first component) separates the plurality of cores (second component) from each other. The material of the sheath also surrounds, or otherwise encases, the plurality of cores. The plurality cores ("islands") and sheath ("sea") extend along the length, or along the entire length, of the fiber, and are integral and inseparable.

The fiber (mono-component or bi-component) may be a melt-spun fiber or a meltblown fiber.

In an embodiment, the fiber (mono-component or bi-component) is a melt-spun fiber. A "melt-spun fiber," as used herein, is a fiber produced by a melt-spinning process. Melt-spinning is a process whereby a polymer melt is extruded through a plurality of fine die capillaries (such as a spinnerette, for example) as molten filaments while simultaneously applying an extensional force which reduces the density of the molten filaments. The molten filaments solidify upon cooling below their melt temperature to form fibers. The term "melt spinning" encompasses staple fiber spinning (including short spinning and long spinning) and bulk continuous filament fiber. Melt-spun fibers may be cold-drawn.

In an embodiment, the fiber is a meltblown fiber. A "meltblown fiber" is a fiber formed by extruding a molten thermoplastic polymer composition through a plurality of fine, usually circular, die capillaries as molten threads or filaments into converging high velocity gas streams (e.g. air) which function to attenuate the threads or filaments to reduced density. The filaments or threads are carried by the high velocity gas streams and deposited on a collecting surface to form a web of randomly dispersed fibers with average thickness generally smaller than 10 microns.

In an embodiment, the fiber has a density with a lower limit of 15 denier and an upper limit of 100 denier.

In an embodiment, the fiber has a ramp-to-break from 2600 meters per minute (mpm) to 3200 mpm.

In an embodiment, the fiber has a tensile strength from 30 g/5 cm, or 50 g/5 cm to 100 g/5 cm.

In an embodiment, the fiber has a tenacity of at least 2 cn/Tex.

The fiber may optionally include one or more other additives. Non-limiting examples of suitable additives include stabilizers, antioxidants, fillers, colorants, nucleating agents, mold release agents, dispersing agents, catalyst deactivator, UV light absorbent, flame retardant, coloring agent, mold release agent, lubricant, anti-static agent, pigment, and any combination of the foregoing.

The present fiber may comprise two or more embodiments disclosed herein.

Fabric

The present disclosure provides a fabric. In an embodiment, the fabric includes a plurality of fibers. The fibers include an odor control component. The odor control component includes: (A) from 85 wt % to 99.5 wt % of an olefin-based polymer and (B) from 15 wt % to 0.5 wt % of an odor suppressant. The odor suppressant is composed of a blend of: (i) an ionomer, (ii) particles of zinc oxide, and (iii) particles of copper oxide.

In an embodiment, the odor control composition has a methyl mercaptan odor suppression value of greater than 45% as measured in accordance with ASTM D5504-12.

A "fabric" is a woven structure or a non-woven structure formed from individual fibers or yarn.

A "woven fabric" is an assembly of interlaced fibers (or yarns). The woven fabric is fabricated by weaving two distinct sets of fibers—the warp fibers (or "warp") and the weft fibers (or "weft"). The warp is the set of fibers in place in a loom before the weft is introduced. The weft is the set of fibers introduced during the weaving process. The lengthwise or longitudinal warp fibers are held stationary in tension on a frame or a loom while the transverse weft fibers are drawn through and inserted over-and-under the warp. The warp and the weft are interlaced at right angles to form the fabric. Non-limiting examples of interlaced woven fabric structures include lock-stitch knitted fabric.

As used herein a "non-woven" or a "non-woven fabric" or "non-woven material" is an assembly of fibers (for example, sheath-core, segmented pie, or "islands-in-the-sea") held together in a random web such as by mechanical interlocking or by fusing at least a portion of the fibers. The non-woven fabrics according to the present disclosure may be fabricated via different techniques. Such methods include, but are not limited to, spunbond process, melt-blowing process, carded web process, air laid process, thermo-calendaring process, adhesive bonding process, hot air bonding process, needle punch process, hydroentangling process, electrospinning process, and combinations thereof.

In an embodiment, the present fabric is produced by way of a spunbond process. In a spunbond process, the fabrication of non-woven fabric includes the following steps: (a) extruding strands of the odor control composition from a spinneret; (b) quenching the strands with a flow of air which is generally cooled in order to hasten the solidification of the molten strands; (c) attenuating the filaments by advancing the filaments through the quench zone with a draw tension that can be applied by either pneumatically entraining the filaments in an air stream or by winding the filaments around mechanical draw rolls of the type commonly used in the textile fibers industry; (d) collecting the drawn strands into a web on a foraminous surface, e.g. moving screen or porous belt; and (e) bonding the web of loose strands into the non-woven fabric. Bonding can be achieved by a variety of means including, but not limited to, thermo-calendaring process, adhesive bonding process, hot air bonding process, needle punch process, hydroentangling process, and combinations thereof.

The spunbond non-woven fabric can be formed into multilayer or laminate structures. Such multilayer structures comprise at least two or more layers, wherein at least one or more layers are spunbond non-woven fabrics according to the present disclosure, and one or more other layers are selected from one or more melt blown non-woven layers, one or more wet-laid non-woven layers, one or more air-laid non-woven layers, one or more webs produced by any non-woven or melt spinning process, one or more film layers, such as cast film, blown film, one or more coating layers derived from a coating composition via, for example, extrusion coating, spray coating, gravure coating, printing, dipping, kiss rolling, or blade coating. The laminate structures can be joined via any number of bonding methods; thermal bonding, adhesive lamination, hydroentangling, needle punching. Structures can range from S to SX, or SXX, or, SXXX, or SXXXX, or SXXXXX, whereby the X can be a film, coating, or other non-woven material in any combination. Additional spunbond layers can be made from the ethylene-based polymer composition, as described herein, and optionally in combinations with one or more polymers and/or additives.

The spunbond non-woven fabric can be used in various end-use applications including, but not limited to, hygiene absorbent products such diapers, feminine hygiene articles, adult incontinence products, wipes, bandages and wound dressings, and disposable slippers and footwear, medical application such isolation gowns, surgical gowns, surgical drapes and covers, surgical scrub suits, caps, masks, and medical packaging.

In the case of staple or binder fibers, the present fibers composed of the odor control composition can be mixed with a variety of other fibers including synthetic fibers such as polyethylene (PE), polypropylene (PP), polyethylene terephthalate (PET), or natural fibers such as cellulose, rayon, or cotton. Such fibers can be wet laid, air laid or carded into a non-woven web. The non-woven web can then be laminated to other materials.

In an embodiment, the plurality of fibers of the non-woven fabric have a diameter from 0.2 microns to 10 microns.

In an embodiment, the present fiber can be used with a carding line to produce fabric.

By way of example, and not limitation, some embodiments of the present disclosure will now be described in detail in the following Examples.

EXAMPLES

Materials used in the examples are provided in Table 1 below.

TABLE 1

| Material/Description | Properties | Source |
| --- | --- | --- |
| Ethylene/octene (LLDPE 1) | 0.9 melt flow rate (I2) (g/10 min) 0.923 g/cc | The Dow Chemical Company |
| ZnO 800HSA Zinc Oxide micro-powder (ZnO-1) | ZnO D50 particle size 3000 nm; density = 5.61 g/cc; Porosity 0.0131 g/m$^3$, surface area 4.46 m$^2$/g | Zinc Oxide, LLC |
| Zinc Oxide micro-powder (ZnO-2) | ZnO D50 particle size 500 nm; density = 5.61 g/cc; Porosity 0.008 m$^3$/g, surface area 3.36 m$^2$/g | 500 nm (US Research Nanomaterials) |
| Zoco102 Zinc Oxide micro-powder (ZnO-3) | ZnO D50 particle size 200 nm; density = 5.61 g/cc; Porosity 0.012 m$^3$/g, surface area 4.4 m$^2$/g | Zochem, Inc. |
| Ampacet 110069 White PE MB Titanium dioxide (TiO$_2$) Masterbatch | 70 wt % TiO$_2$ in Carrier Resin LLDPE (MI 2.3, d- 0.917 g/cc) Masterbatch Specific gravity: 2.03 | Ampacet Corporation |
| Surlyn ® 9150 (Zinc Ionomer) | Ethylene/Methacrylic Acid Copolymer, zinc cation Density 0.970 g/cc, melt flow 4.5 g/10 min | Dow-DuPont |
| Cu$_2$O | 325 mesh | Reade Advanced Materials |

1. Films

Master batch processing. Two master batches were prepared to ease feeding the odor suppressing compositions into a subsequent film line. The master batches were prepared on a Coperion ZSK 26 twin screw extruder using a general purpose screw. The residence time of material was controlled by the screw design, feed rate of 20 lbs/hr, and a screw speed of 300 revolutions per minute (RPM). No oil was injected. There was no side arm feeder. No vacuum was pulled. The compounded material was sent through a water bath before being cut by a strand cut pelletizer. After collection the pelletized materials were N$_2$ purged, then sealed in an aluminum bag.

The composition of the first master batch (MB1) was 50 wt % LLDPE 1, 25 wt % ZnO, and 25 wt % Surlyn 9150. The composition of the second master batch (MB2) was 90 wt % LLDPE 1 and 10 wt % Cu$_2$O. Examples and counter example formulations were generated using the appropriate amount of pure LLDPE 1, MB1 and MB2 to achieve the target weight % of each composition listed.

TABLE 2

Blown film line process parameters

| Parameter | Units | Films without TiO$_2$ MB | Films containing TiO$_2$ MB |
|---|---|---|---|
| Takeoff | m/min | 15 | 15 |
| Layflat | cm | 23.5 | 23.5 |
| Frostline | cm | 14 | 14 |
| B.U.R | ratio | 2.5 | 2.5 |
| Die gap | mm | 2.0 | 2.0 |
| Melt temperature - Ext. A | ° C. | 218 | 218 |
| Melt temperature - Ext. B | ° C. | 226 | 226 |
| Melt temperature - Ext. C | ° C. | 215 | 215 |
| RPM - Ext. A | rpm | 51 | 51 |
| RPM - Ext. B | rpm | 50 | 50 |
| RPM - Ext. C | rpm | 32 | 32 |
| Total Output | kg/hr | 8.8 | 8.8 |
| Film Total Thickness | mm | 0.023 | 0.056 |

2. Odor Suppression

The compositions of comparative samples (CS) and inventive examples (IE) are shown in Table 3.

The odor suppression values (OSV) for are provided in Table 3 below. Concentrations were measured using the reference sample (CS 1) as the calibration standard after two days, concentrations in the reference sample might change after two days, so the concentrations in the samples should be considered as the relative change to the reference sample.

TABLE 3

Odor Suppression Values and Blown Film Properties
OSV of Methyl Mercaptan

| Sample | Components | Methyl Mercaptan OSV (%) |
|---|---|---|
| CS 1 | 99% LLDPE 1 + 1% TiO$_2$ MB | 12 |
| CS 2 | 97.5% LLDPE 1 + 2.5% TiO$_2$ MB | 2 |
| CS 3 | 99% LLDPE 1 + 0.5 wt % ZnO + 0.5 wt % Zinc Ionomer | 28 |
| CS 4 | 97.5% LLDPE 1 + 1.25 wt % ZnO + 1.25 wt % Zinc Ionomer | 44 |
| IE 1 | 97.4% LLDPE 1 + 1.25 wt % ZnO + 1.25 wt % Zinc Ionomer + 0.1% Cu$_2$O | 80 |
| IE 2 | 98.9% LLDPE 1 + 0.5 wt % ZnO + 0.5 wt % Zinc Ionomer + 0.1% Cu$_2$O | 64 |
| IE 3 | 99.4% LLDPE 1 + 0.25 wt % ZnO + 0.25 wt % Zinc Ionomer + 0.1% Cu$_2$O | 49 |

Zinc ionomer used in Table 3 is Surlyn 9150
*TiO$_2$ MB—titanium dioxide masterbatch 70 wt % TiO$_2$ powder in 30 wt % LLDPE carrier, added for white color In Table 3, component amounts for each sample yield 100 wt % total sample composition. It can readily be observed that the ZnO/zinc ionomer combination is effective in improving OSV as compared to a composition that lacks any odor suppressing technology by comparing the OSV for CS 3 (28%) to the OSVs for CS 1 & 2 (12% and 2% respectively). However, it is surprising to see that although Cu$_2$O is added at very low loadings as part of the present odor suppressant (i.e., at <10% of the combination of ZnO, zinc ionomer, and Cu$_2$O in IE2), it can further improve the OSV to 64% as compared to CS 3 OSV of 28%, (i.e., the sample with zinc ionomer and ZnO, and without Cu$_2$O present). The addition of Cu$_2$O unexpectedly allows for a reduction in ZnO/zinc ionomer concentrations by 50% in the composition while maintaining an OSV that is almost 50% higher than the ZnO/zinc ionomer combination that does not have Cu$_2$O present, as can be observed by comparing the OSV for 1E3 (49%) to the OSV of CS3 (28%). It is further observed that the ZnO/zinc ionomer combination still exhibits a significant influence on OSV in that higher loadings of these materials in combination with 0.1 wt % Cu$_2$O exhibits the highest OSV of the inventive examples 1E1 (80%) and IE2 (64%) shown in Table 3.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A fiber comprising:
an odor control composition, the odor control composition comprising:
(A) from 85 wt % to 99.5 wt % of an olefin-based polymer
(B) from 15 wt % to 0.5 wt % of an odor suppressant comprising a blend of:
(i) an ionomer;
(ii) particles of zinc oxide; and
(iii) particles of copper oxide.

2. The fiber of claim 1 wherein the odor control composition has a methyl mercaptan odor suppression value of greater than 45% as measured in accordance with ASTM D5504-12.

3. The fiber of claim 1, wherein the olefin-based polymer is an ethylene/alpha-olefin copolymer.

4. The fiber of claim 1 wherein the ionomer is a zinc salt of a polymer selected from the group of ethylene/methylmethacrylic acid, ethylene/vinyl acrylic acid, ethylene/methacrylate, ethylene/n-butyl acrylic acid, and ethylene acrylic acid.

5. The fiber of claim 1, wherein the ionomer is a zinc ionomer.

6. The fiber of claim 1, wherein the particles of zinc oxide have a D50 particle size from 100 nm to 3000 nm.

7. The fiber of claim 1, wherein the particles of zinc oxide have
a surface area from 1 m$^2$/g to 9 m$^2$/g; and
a porosity less than 0.020 m$^3$/g.

8. The fiber of claim 1, wherein the particles of copper oxide are selected from the group of copper (I) oxide and copper (II) oxide.

9. The fiber of claim 1, wherein a weight percent ratio between the ionomer (Bi) the zinc oxide (Bii) and the copper oxide (Biii) is from 150:100:1 to 2.9:2.5:1.

10. The fiber of claim 1 wherein the fiber is a monocomponent fiber.

11. The fiber of claim 1 wherein the fiber is a bi-component fiber comprising:
a first component that is the odor control composition;
a second component that is a polymeric material different than the odor control composition.

12. The fiber of claim 11 wherein the bi-component fiber has a sheath-core structure.

13. The fiber of claim 11 wherein the first component is present in a sheath.

14. A fabric comprising:
a plurality of fibers, the fibers comprising
an odor control composition, the odor control composition comprising
(A) from 85 wt % to 99.5 wt % of an olefin-based polymer
(B) from 15 wt % to 0.5 wt % of an odor suppressant comprising a blend of:
  (i) an ionomer;
  (ii) particles of zinc oxide; and
  (iii) particles of copper oxide.

15. The fabric of claim 14 wherein the odor control composition has a methyl mercaptan odor suppression value of greater than 45% as measured in accordance with ASTM D5504-12.

* * * * *